(12) United States Patent  
Taimisto

(10) Patent No.: US 7,063,696 B2
(45) Date of Patent: Jun. 20, 2006

(54) EPICARDIAL MYOCARDIAL REVASCULARIZATION AND DENERVATION METHODS AND APPARATUS

(75) Inventor: Miriam H. Taimisto, San Jose, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 187 days.

(21) Appl. No.: 10/693,368

(22) Filed: Oct. 23, 2003

(65) Prior Publication Data

US 2004/0082949 A1 Apr. 29, 2004

Related U.S. Application Data

(62) Division of application No. 09/618,687, filed on Jul. 18, 2000, now Pat. No. 6,669,691.

(51) Int. Cl.
  *A61B 18/14* (2006.01)
  *A61B 18/12* (2006.01)
(52) U.S. Cl. .................................. 606/41; 128/898
(58) Field of Classification Search ................ 128/898; 606/41
See application file for complete search history.

(56) References Cited

U.S. PATENT DOCUMENTS

| 4,565,200 | A |   | 1/1986  | Cosman            |       |
|-----------|---|---|---------|-------------------|-------|
| 5,007,908 | A |   | 4/1991  | Rydell            |       |
| 5,255,678 | A |   | 10/1993 | Deslauriers et al.|       |
| 5,281,218 | A |   | 1/1994  | Imran             |       |
| 5,403,311 | A |   | 4/1995  | Abele             |       |
| 5,431,649 | A |   | 7/1995  | Mulier            |       |
| 5,472,441 | A |   | 12/1995 | Edwards           |       |
| 5,554,152 | A | * | 9/1996  | Aita et al. ..... | 606/7 |
| 5,630,426 | A |   | 5/1997  | Eggers            |       |
| 5,672,153 | A |   | 9/1997  | Lax et al.        |       |
| 5,683,366 | A |   | 11/1997 | Eggers et al.     |       |
| 5,700,259 | A |   | 12/1997 | Negus et al.      |       |
| 5,707,349 | A |   | 1/1998  | Edwards           |       |
| 5,792,140 | A |   | 8/1998  | Tu et al.         |       |
| 5,800,484 | A |   | 9/1998  | Gough             |       |
| 5,807,395 | A |   | 9/1998  | Mulier            |       |
| 5,817,092 | A |   | 10/1998 | Behl              |       |
| 5,824,005 | A | * | 10/1998 | Motamedi et al. ..| 606/15|
| 5,832,929 | A |   | 11/1998 | Rudko et al.      |       |
| 5,860,951 | A |   | 1/1999  | Eggers et al.     |       |
| 5,873,855 | A |   | 2/1999  | Eggers et al.     |       |
| 5,876,330 | A |   | 3/1999  | Grabover et al.   |       |
| 5,921,982 | A |   | 7/1999  | Lesh              |       |
| 5,938,632 | A |   | 8/1999  | Ellis             |       |
| 5,944,716 | A |   | 8/1999  | Hektner           |       |
| 5,947,964 | A |   | 9/1999  | Eggers            |       |
| 5,964,757 | A |   | 10/1999 | Ponzi             |       |
| 5,976,164 | A |   | 11/1999 | Bencini et al.    |       |
| 5,997,525 | A |   | 12/1999 | March et al.      |       |

(Continued)

FOREIGN PATENT DOCUMENTS

EP 0628288 A2 12/1994

(Continued)

*Primary Examiner*—Michael F Peffley
*Assistant Examiner*—Henry M Johnson, III
(74) *Attorney, Agent, or Firm*—Henricks, Slavin & Holmes LLP

(57) ABSTRACT

Electrophysiological methods and apparatus are disclosed. An exemplary myocardial treatment method includes the steps of positioning an electrode on the epicardial surface of a ventricle and transmitting energy from the electrode, through the epicardial surface and into the ventricular wall to create a lesion within the ventricular wall. An exemplary apparatus includes a shaft and one or more electrodes that have a main portion and a needle portion.

11 Claims, 6 Drawing Sheets

U.S. PATENT DOCUMENTS

| | | |
|---|---|---|
| 6,010,476 A | 1/2000 | Saadat |
| 6,019,756 A | 2/2000 | Mueller et al. |
| 6,030,382 A | 2/2000 | Fleischman et al. |
| 6,053,924 A | 4/2000 | Hussein |
| 6,053,937 A | 4/2000 | Edwards et al. |
| 6,056,743 A | 5/2000 | Ellis et al. |
| 6,063,082 A | 5/2000 | DeVore et al. |
| 6,066,131 A | 5/2000 | Mueller et al. |
| 6,080,163 A | 6/2000 | Hussein et al. |
| 6,086,534 A | 7/2000 | Keston |
| 6,093,185 A | 7/2000 | Ellis et al. |
| 6,102,046 A | 8/2000 | Weinstein et al. |
| 6,106,521 A | 8/2000 | Blewett et al. |
| 6,117,130 A | 9/2000 | Kung |
| 6,120,520 A | 9/2000 | Saadat et al. |
| 6,132,422 A | 10/2000 | Rudko |
| 6,152,918 A * | 11/2000 | Padilla et al. ............. 606/15 |
| 6,152,920 A | 11/2000 | Thompson et al. |
| 6,165,172 A | 12/2000 | Farley et al. |
| 6,212,433 B1 | 4/2001 | Behl |
| 6,237,605 B1 * | 5/2001 | Vaska et al. ............. 128/898 |
| 6,283,935 B1 | 9/2001 | Laufer et al. |
| 6,286,512 B1 * | 9/2001 | Loeb et al. ............. 128/898 |
| 6,287,297 B1 | 9/2001 | Woodruff et al. |
| 6,314,963 B1 * | 11/2001 | Vaska et al. ............. 128/898 |
| 6,358,246 B1 | 3/2002 | Behl et al. |
| 6,474,340 B1 * | 11/2002 | Vaska et al. ............. 128/898 |
| 6,527,767 B1 * | 3/2003 | Wang et al. ............. 606/32 |
| 6,666,863 B1 * | 12/2003 | Wentzel et al. ............. 606/41 |
| 6,669,691 B1 | 12/2003 | Taimisto |

FOREIGN PATENT DOCUMENTS

| | | |
|---|---|---|
| WO | WO 97/30644 A1 | 8/1997 |
| WO | WO 99/07296 A1 | 2/1999 |
| WO | WO 00/13602 A2 | 3/2000 |

* cited by examiner

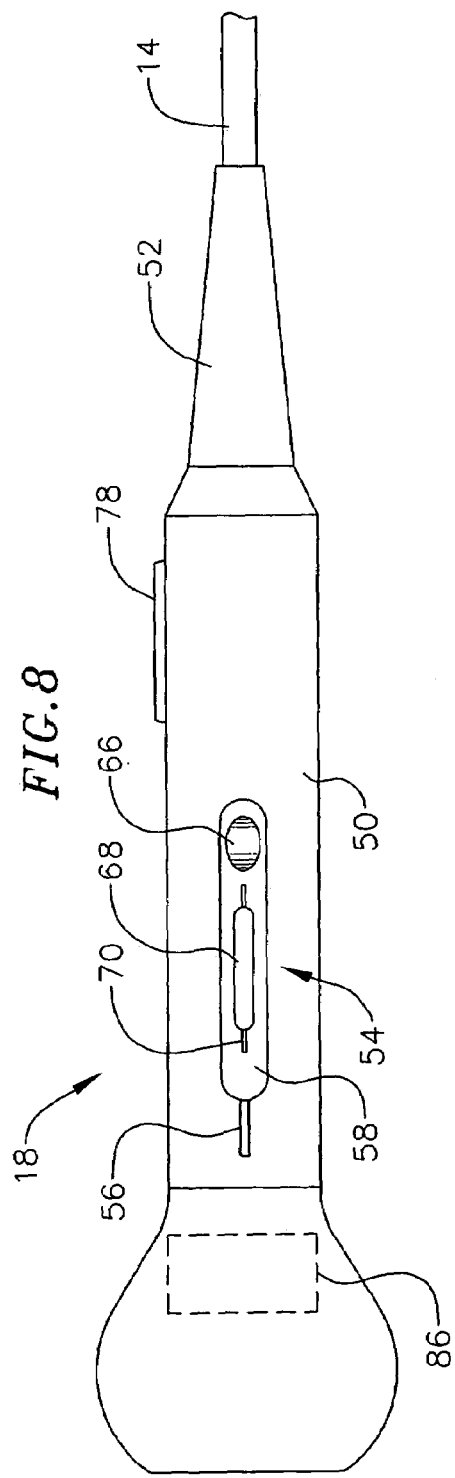
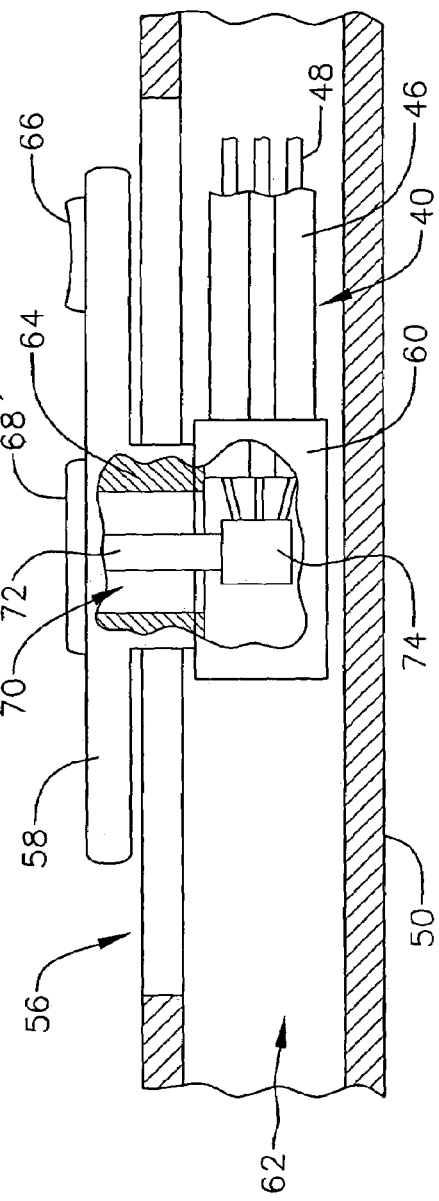

EPICARDIAL MYOCARDIAL REVASCULARIZATION AND DENERVATION METHODS AND APPARATUS

This application is a divisional of U.S. application Ser. No. 09/618,687, filed Jul. 18, 2000, now U.S. Pat. No. 6,669,691.

BACKGROUND OF THE INVENTIONS

1. Field of Inventions

The present inventions relate generally to the treatment of the heart and, more particularly to treatments that, among other things, stimulate angiogenesis and relieve angina.

2. Description of the Related Art

Atherosclerosis, which is a leading causes of death, occurs when plaque develops at various locations within the arterial system, thereby restricting the flow of blood through the affected vessels. When atherosclerosis occurs within the blood vessels that supply blood to the muscles of the heart, myocardial infarctions, ischemia and/or angina can result due to the reduction in blood flow.

A variety of myocardial revascularization techniques have been developed in recent years in an attempt to increase the flow of blood into the heart muscle and to stimulate angiogenesis, i.e. the creation of new blood vessels within the heart muscle. In percutaneous myocardial revascularization (PMR), which is also referred to as direct myocardial revascularization (DMR), channels are formed in the endocardial surface with catheter-based devices. The PMR and DMR channels extend partially through the ventricular wall. Transmyocardial revascularization (TMR), on the other hand, involves the formation of channels that extend completely through the ventricular wall. Although the use of mechanical piercing and cutting devices has been proposed, the revascularization channels are typically formed with a laser device or the combination of mechanical and laser devices. Radiofrequency energy delivered through an electrode has also been used to create craters on the endocardial surface.

Although they have proven to be useful, the inventor herein has determined that there are a number of shortcomings associated with conventional myocardial revascularization techniques. For example, the creation of channels through the ventricular wall during TMR is a relatively time consuming procedure and additional time is required to stop the bleeding associated with the procedure. A single channel takes about three to five seconds to create and pressure must be applied to the channel (usually with a finger) for one to two minutes in order to give the blood time to clot and stop the bleeding. The TMR procedure also requires a relatively invasive muscle-sparing thoracotomy to access the heart and results in measurable blood loss (typically about 200–300 cc). Moreover, the pulse or continuous wave energy applied to the tissue during laser-based PMR, DMR or TMR can entrain the patient's heart rhythm and cause fibrillation or tachycardia.

Cardiac denervation, which provides relief from angina pain, is a beneficial side effect of the aforementioned myocardial revascularization techniques. Patients experience pain relief because some of the nervous tissue in the ventricular wall is destroyed during the channel formation process. The present inventor has, however, determined that the level of cardiac denervation achieved by conventional myocardial revascularization techniques is susceptible to improvement. For example, the cross-sectional area of the channels is relatively small, which limits the volume of nervous tissue that is destroyed by the channels. PMR and DMR techniques are further hampered by the fact that the nervous tissue is concentrated close to the epicardial surface. PMR and DMR channels, which extend through the endocardial surface and only partially through the ventricular wall, fail to reach the region closer to the epicardial surface that contains the higher concentration of nervous tissue.

SUMMARY OF THE INVENTION

Accordingly, the general object of the present inventions is to provide methods and apparatus that avoid, for practical purposes, the aforementioned problems. In particular, one object of the present inventions is to provide methods and apparatus for stimulating angiogenesis that can be performed more quickly, and with less bleeding, than conventional PMR, DMR and TMR techniques. Another object of the present inventions is to provide methods and apparatus for stimulating angiogenesis that will not cause fibrillation or tachycardia. Still another object of the present inventions is to provide methods and apparatus for myocardial revascularization that destroy larger volumes of nervous tissue than conventional PMR, DMR and TMR techniques.

In order to accomplish some of these and other objectives, a myocardial treatment method in accordance with one embodiment of a present invention includes the steps of positioning an electrode on the epicardial surface of a ventricle and transmitting energy from the electrode, through the epicardial surface and into the ventricular wall to create a lesion within the ventricular wall. With respect to apparatus, an apparatus in accordance with one embodiment of a present invention includes a shaft and one or more electrodes that have a main portion and a needle portion. The electrode main and needle portions are constructed and arranged relative to one another such that the electrode main portion will rest on the surface of a body structure, such as a ventricle, when the electrode needle portion penetrates the body structure.

There are a number of advantages associated with the present methods and apparatus. In the area of myocardial revascularization, for example, the present surgical probe may be used in a procedure in accordance with the present method to form a lesion with a relatively large portion at and near the epicardial surface. The electrode needle portion may be used to form a relatively small lesion portion below the relatively large portion. Preferably, the needle portion is movable, which allows the physician to selectively after its depth to achieve the desired levels of additional lesion formation. The thermally damaged area (i.e. the area in which the lesion is formed) will stimulate angiogenesis. In contrast to PMR, DMR and TMR procedures, which require time consuming channel formation, a suitable epicardial lesion pattern may be created quickly. A lesion creation procedure in which, for example, 20 lesions are created will typically take about 10 minutes to complete, as compared to 30 minutes for typical PMR and DMR procedures where 20 channels are created and 60 minutes for a typical TMR procedure where 20 channels are created. The formation of epicardial lesions is also superior to PMR, DMR and TMR procedures because it does not cause the bleeding that occurs during channel formation.

The present methods and apparatus also destroy nervous tissue, and provide angina relief, in a manner that is more efficient than PMR, DMR and TMR procedures. As noted above, nervous tissue is concentrated near the epicardial surface. The formation of lesions that have a relatively large lesion portion at and near the epicardial surface will, therefore, result in far more cardiac denervation and angina relief than that which can realized through the formation of channels that have small cross-sectional areas and, in the case of PMR and DMR in particular, channels that do not reach the portion of ventricular wall with the higher concentrations of nervous tissue.

A preferred implementation of the present apparatus includes a relatively short shaft that facilitates use of the apparatus in thoracoscopic procedures. As such, the electrode (or electrodes) may be visually guided to the desired location on the epicardial surface. This is easier and less time consuming than manipulating the distal end of a relatively long endovascular catheter to position a channel or crater forming device on the endocardial surface, as is the case with PMR and DMR procedures. Thoracoscopic procedures are also less invasive than the muscle-sparing thoracotomy associated with TMR procedures.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 8 is a plan view of a handle in accordance with a preferred embodiment of a present invention.

FIG. 9 is a side, partial section, partial cutaway view a portion of the handle illustrated in FIG. 8.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions. Additionally, this specification discloses various structures in the context of cardiac treatment because the structures are well suited for use with myocardial tissue and can produce intimate tissue contact with epicardial tissue. One application is the creation of lesions on and below the epicardial surface to stimulate angiogenesis. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus and other solid organs.

Figure 1:
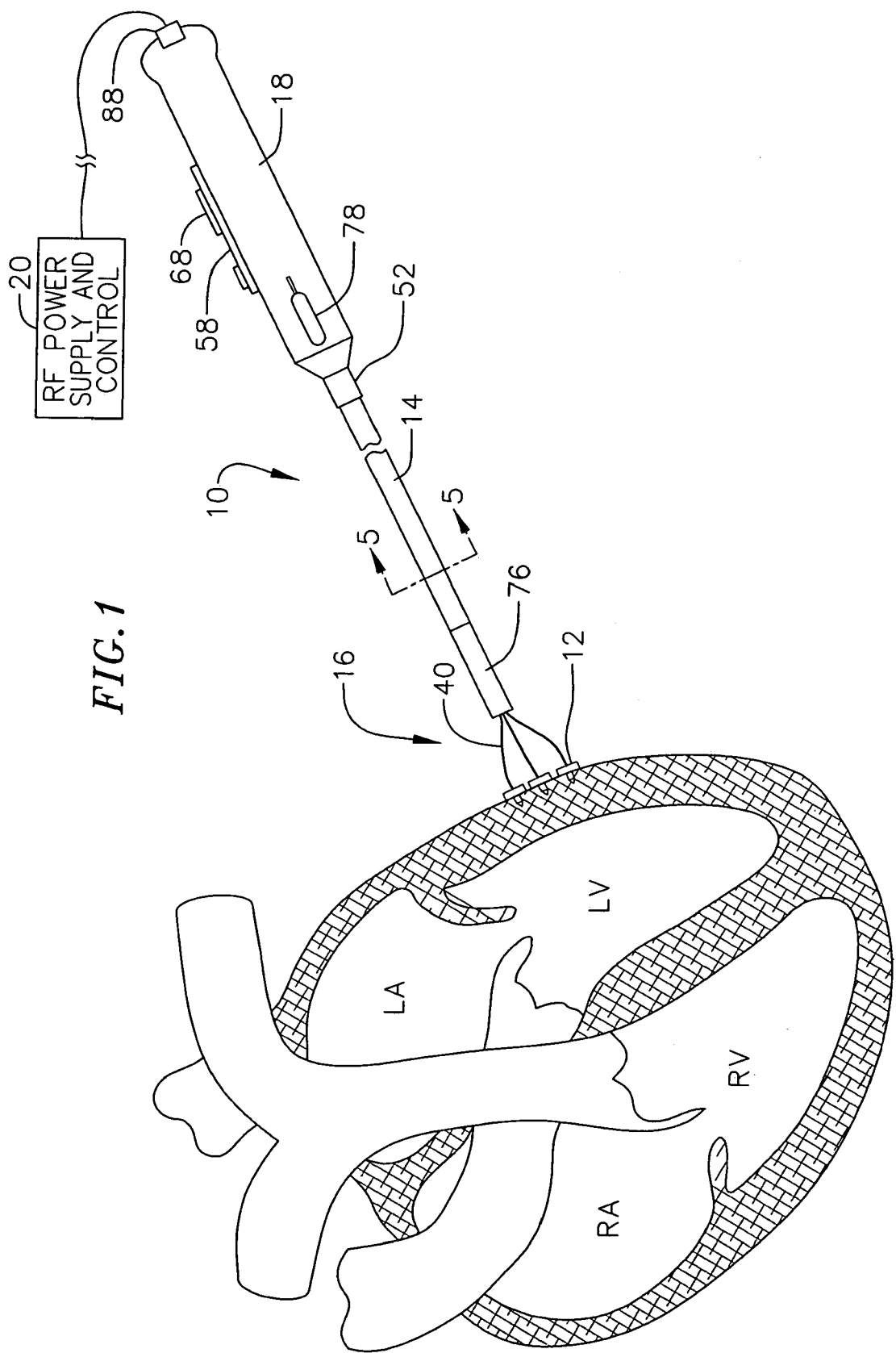
FIG. 1 is a schematic, partial section view of a human heart and a side view of an apparatus in accordance with a preferred embodiment of the present invention.
Figure 2:
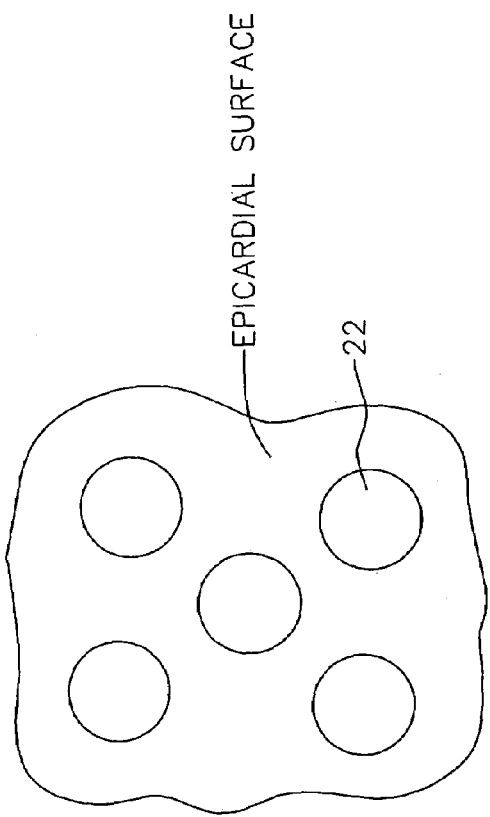
FIG. 2 is a plan view showing an exemplary epicardial lesion pattern that may be formed with the exemplary apparatus illustrated in FIG. 1.

As illustrated for example in FIGS. 1 and 2, a surgical probe 10 for positioning one or more electrodes 12 within a patient includes a relatively short shaft 14 and a structure, such as a bendable electrode support assembly 16, associated with the distal end of the shaft for supporting the electrodes. The proximal end of the shaft is secured to a handle 18 that may be connected to a power supply and control device 20 in the manner described below. In the exemplary embodiment, the electrode support assembly 16 supports five (5) electrodes 12 in such a manner that the electrodes will produce lesions 22 in the pattern illustrated in FIG. 2.

Figure 3:
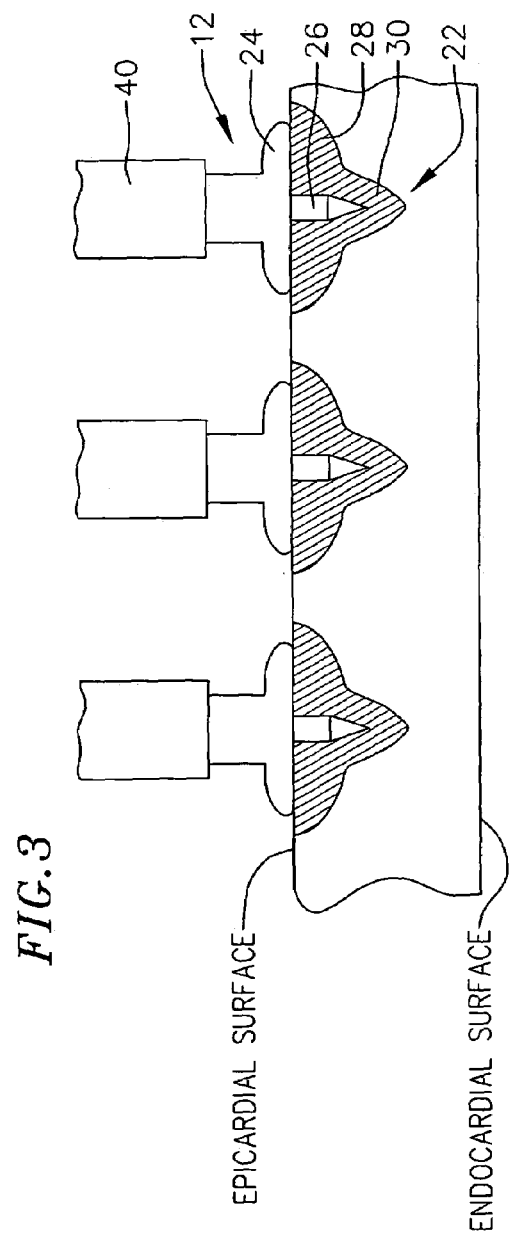
FIG. 3 is a side, partial section view showing the formation of lesions on and beneath the epicardial surface with the exemplary apparatus illustrated in FIG. 1.
Figure 4:
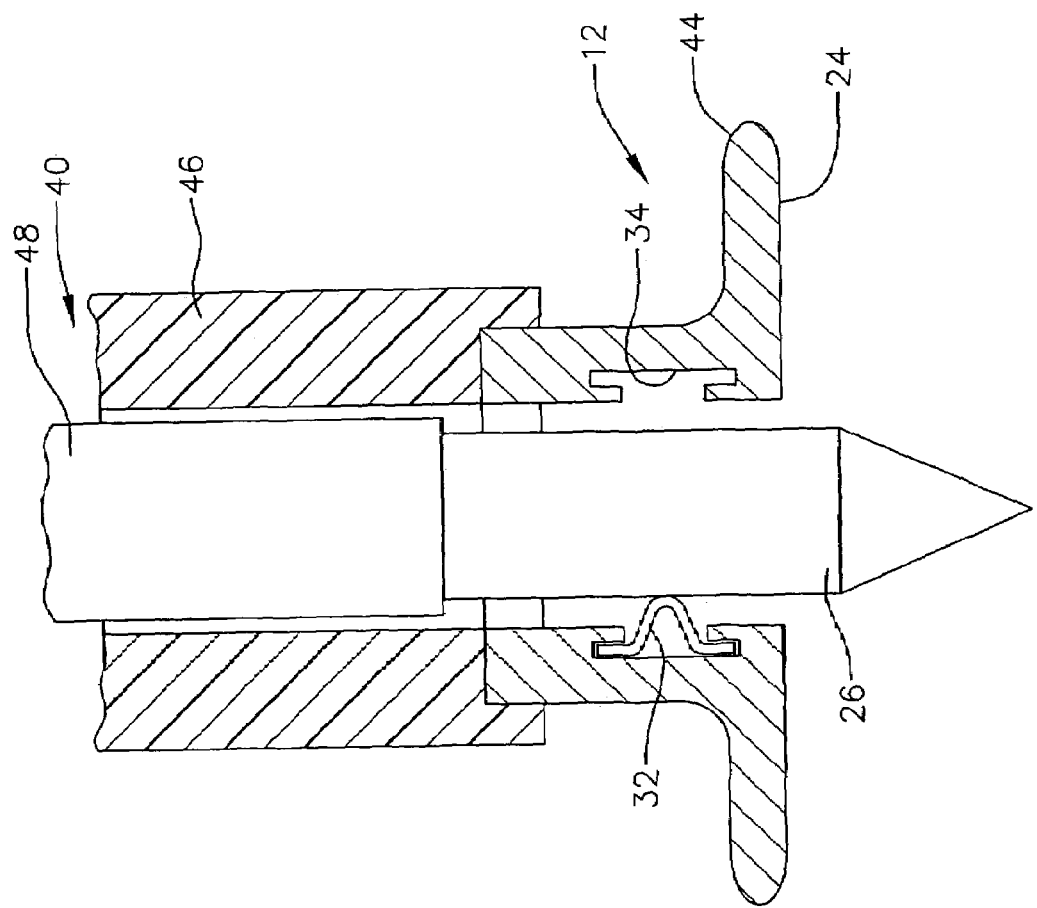
FIG. 4 is a side, partial section view of an electrode in accordance with a preferred embodiment of a present invention.

The exemplary electrodes 12, which are illustrated in greater detail in FIGS. 3 and 4, include a main portion 24, which is adapted to engage the epicardial surface, and a needle portion 26, which is adapted to pierce the epicardial surface and contact tissue within the ventricular wall. As such, the lesions 22 have a relatively large region 28 at and near the epicardial surface and a smaller region 30 that extends deeper into the ventricular wall. In addition to the stimulation of angiogenesis associated with the formation of lesions 22, locating the largest volumetric regions of the lesions (i.e. regions 28) at and near the epicardial surface, which is the location of the high concentrations of nervous tissue, provides more efficient denervation than that which is realized through conventional revascularization methods. The electrode main portion 24 and needle portion 26 are preferably separate structural elements so that the needle portion may be moved relative to main portion, thereby allowing the physician to selectively alter the magnitude of the needle portion penetration and the size of the smaller region 30. Although other configurations may be employed, the electrode main portion 24 and needle portion 26 are circular in cross-section.

The electrode main portion 24 and needle portion 26 may be formed from electrically conducting material, such as copper alloy, platinum, and stainless steel. The electrically conducting material may also be coated with platinum-iridium or gold to improve its conduction properties and biocompatibility. In the exemplary embodiment, which maybe used to create lesions on the epicardial surface, the diameter of the electrode main portion 24 is about 1.5 to 5.0 mm, while the diameter of the needle portion 26 is about 0.5 to 1.0 mm, which is small enough to prevent the formation of channels. The diameters of the electrode main and needle portions 24 and 26 may, however, range from 0.5 to 10.0 mm and 0.3 to 2.0 mm in other applications.

The electrode needle portions 26 are electrically connected to the power supply and control device 20 (as described below) and each electrode needle portion is electrically connected to the corresponding main portion 24 by a flexible contactor 32. The flexible contactor 32, which may be formed from a resilient, conductive material such as 17-7PH stainless steel (spring steel), is mounted within a recess 34 located within the inner surface of the main portion 24. The length of the flexible contactor 32 should be sufficient to provide an effective electrical contact area and sufficient mechanical support for its spring-like behavior. The flexible contactor 32 in the exemplary embodiment will be about 2.5 mm in length and, therefore, will extend around the main portion for about 60°. Alternatively, the electrode main portions 24 may be connected to the power supply and control device 20. In either case, the flexible contactor 32 insures that electrical contact is maintained between the electrode main portion 24 and needle portion 26 despite the movement of the needle portion relative to the main portion.

The relatively short shaft 14 consists of a hypotube 36 with an outer polymer coating 38 (FIG. 5) and is between approximately 4 and 18 inches in length. Preferably, the shaft 14 is 8 inches in length with an outer diameter between approximately 6 and 24 French. Because force is applied through the shaft 14, the shaft 14 should be sufficiently strong to prevent collapse and is preferably relatively stiff. As used herein the phrase "relatively stiff" means that the shaft 14 is either rigid or malleable. A rigid shaft cannot be bent. A malleable shaft can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. Rigid shafts are preferably formed from stainless steel, while malleable shafts may be formed from annealed stainless steel.

One method of quantifying the flexibility of a shaft, be it shafts in accordance with the present inventions or the shafts of conventional catheters, is to look at the deflection of the shaft when one end is fixed in cantilever fashion and a force normal to the longitudinal axis of the shaft is applied somewhere between the ends. Such deflection (σ) is expressed as follows:

$$\sigma = WX^2(3L-X)/6EI$$

where:
  W is the force applied normal to the longitudinal axis of the shaft,
  L is the length of the shaft,
  X is the distance between the fixed end of the shaft and the applied force,
  E is the modulus of elasticity, and
  I is the moment of inertia of the shaft.

When the force is applied to the free end of the shaft, deflection can be expressed as follows:

$$\sigma = WL^3/3EI$$

Assuming that W and L are equal when comparing different shafts, the respective E and I values will determine how much the shafts will bend. In other words, the stiffness of a shaft is a function of the product of E and I. This product is referred to herein as the "bending modulus." E is a property of the material that forms the shaft, while I is a function of shaft geometry, wall thickness, etc. Therefore, a shaft formed from relatively soft material can have the same bending modulus as a shaft formed from relatively hard material, if the moment of inertia of the softer shaft is sufficiently greater than that of the harder shaft.

For example, a malleable relatively stiff 2 inch shaft would have a bending modulus of at least approximately 1 lb.-in.$^2$ and, preferably, between approximately 3 lb.-in.$^2$ and approximately 50 lb.-in.$^2$. By comparison, 2 inch piece of a conventional catheter shaft, which must be flexible enough to travel through veins, typically has bending modulus between approximately 0.1 lb.-in.$^2$ and approximately 0.3 lb.-in.$^2$. It should be noted that the bending modulus ranges discussed here are primarily associated with initial deflection. In other words, the bending modulus ranges are based on the amount of force, applied at and normal to the free end of the longitudinal axis of the cantilevered shaft, that is needed to produce 1 inch of deflection from an at rest (or no deflection) position.

As noted above, the deflection of a shaft depends on the composition of the shaft as well as its moment of inertia. The shaft could be made of elastic material, plastic material, elasto-plastic material or a combination thereof. By designing the shaft 14 to be relatively stiff (and preferably malleable), the present surgical probe is better adapted to the constraints encountered during the surgical procedure. The force required to bend a relatively stiff 2 inch long shaft should be in the range of approximately 1.5 lbs. to approximately 12 lbs. By comparison, the force required to bend a 2 inch piece of conventional catheter shaft should be between approximately 0.2 lb. to 0.25 lb. Again, such force values concern the amount of force, applied at and normal to the free end of the longitudinal axis of the cantilevered shaft, that is needed to produce 1 inch of deflection from an at rest (or no deflection) position.

Ductile materials are preferable in many applications because such materials can deform plastically before failure due to fracturing. Materials are classified as either ductile or brittle, based upon the percentage of elongation when the fracture occurs. A material with more than 5 percent elongation prior to fracture is generally considered ductile, while a material with less than 5 percent elongation prior to fracture is generally considered brittle. Material ductility can be based on a comparison of the cross sectional area at fracture relative to the original cross area. This characteristic is not dependent on the elastic properties of the material.

Alternatively, the shaft 14 could be a mechanical component similar to shielded (metal spiral wind jacket) conduit or flexible Loc-Line®, which is a linear set of interlocking ball and socket linkages that can have a center lumen. These would be hinge-like segmented sections linearly assembled to make the shaft.

Figure 6:
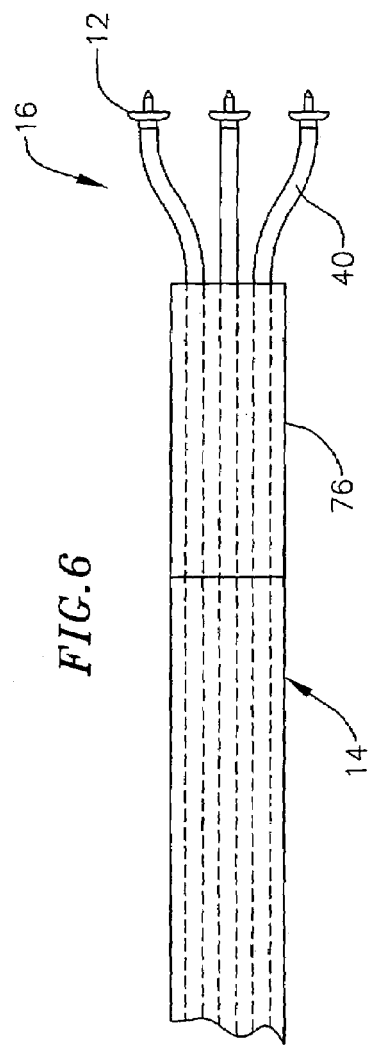
FIG. 6 is a side view of the distal portion of an apparatus illustrated in FIG. 1 with the electrode support assembly extended.

As illustrated for example in FIGS. 4–7, the exemplary electrode support assembly 16 consists of five electrode support elements 40 that are movable between a storage position within the shaft 14 and a use position beyond the distal end of the shaft that locates the electrodes 12 on the epicardial surface. The support elements 40 are arranged in the exemplary embodiment such that the electrodes 12 will produce the lesion pattern illustrated in FIG. 2. Referring more specifically to FIG. 6, four of the support elements 40 are pre-shaped such that their respective distal portions will bend radially outwardly when extended beyond the distal end of the shaft 14. The electrodes 12 on these support elements 40 will form the outer four lesions 22 in the pattern illustrated in FIG. 2. The distal portion of the fifth, and central, support element 40 will remain linear when extended beyond the distal portion of the shaft 14. Other electrode support assemblies, such as assemblies that include from one to ten support elements and/or those that produce linear or curvilinear patterns of spaced lesions or other patterns different than the pattern illustrated in FIG. 2, may also be used.

The electrode support assembly 16 is preferably about 10 mm in diameter and about 60 mm in length measured from the electrodes 12 to the distal end of the shaft 14 when the support assembly is in the fully extended position. The individual electrode support elements 40 are constructed and arranged such that there will be a space of about 1.5 to 2.1 cm between the electrodes 12 that form the outer four lesions in the pattern illustrated in FIG. 2 and a space of about 0.5 to 1.0 cm between each of those electrodes and the center electrode.

Figure 7:
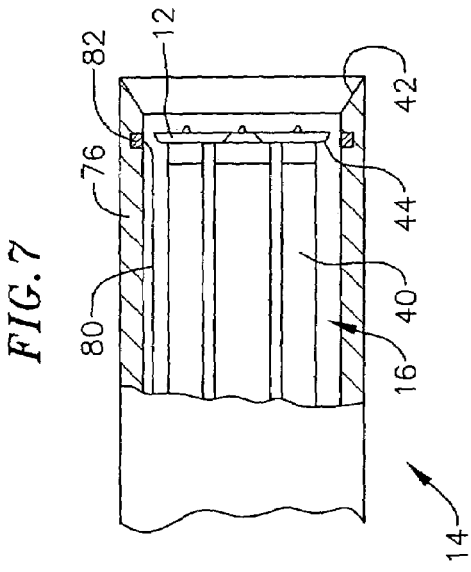
FIG. 7 is a side, partial cutaway view of the distal portion of an apparatus illustrated in FIG. 1 with the electrode support assembly retracted.

Referring more specifically to FIG. 7, the distal end of the tip section 76 (discussed below) preferably includes a beveled surface 42 and the electrode main portions 24 preferably include curved surfaces 44. These surfaces facilitate passage of the electrodes 12 in to and out of the distal opening in the tip section 76.

Figure 5:
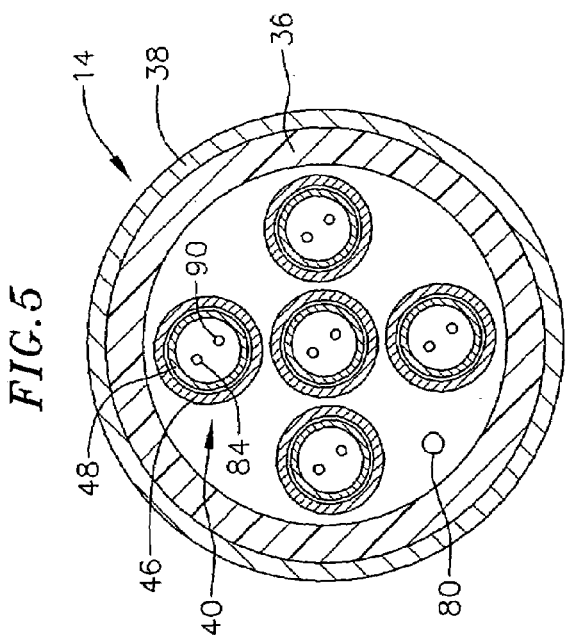
FIG. 5 is a section view taken along line 5—5 in FIG. 1.

In the exemplary embodiment, the electrode support elements 40 consist of a tubular main support element 46, on which the electrode main portion 24 is supported, and a tubular needle support element 48, on which the electrode needle portion 26 is supported. [Note FIG. 5.] The needle support elements 48 are movable relative to the main support elements 46. The main support elements 46 are preferably formed from resilient, inert shape memory material such as nickel titanium (commercially available as Nitinol material), 17-7 stainless steel, or resilient injection molded inert plastic and are covered by suitable biocompatible thermoplastic or elastomeric material such as Pebax® or Pellethane®. The needle support elements 48 are preferably formed from a flexible insulative material, such as Kynar®, that allows the needle support elements to be advanced distally and proximally when the main support elements 40 are in the extended, bent orientation illustrated in FIG. 6.

The proximal ends of the electrode support elements 40, as well as the proximal end of the shaft 14, are secured to the handle 18. As illustrated for example in FIGS. 8 and 9, the exemplary handle 18 includes a handle body 50, a strain relief element 52 and a control apparatus 54 that is slidably mounted within a slot 56 in the handle body. The control apparatus 54 includes a slidable tab 58, a tubular member 60 located within the hollow handle body interior 62, and a post 64 that passes through the slot 56 and connects the slidable tab to the tubular member. The proximal ends of the electrode support members 40 are secured within the tubular member 60 and, as a result, the physician can move the electrode support members distally and proximally by moving the slidable tab 58. To that end, the slidable tab 58 includes a thumb rest 66.

The exemplary control apparatus 54 may also be used to move the electrode needle portions 26 distally and proximally relative to the electrode main portions 24. More specifically, a slidable tab 68 is located adjacent to a slot 70 formed in the slidable tab 58. A post 72 extends inwardly from the slidable tab 68 to an anchor 74. The proximal ends of the needle portion support elements 48 are secured to the anchor 74. So configured, movement of the slidable tab 68 relative to the slidable tab 58 will cause the electrode needle portion support elements 48 to move relative to the electrode main portion support elements 46 and, correspondingly, the electrode needle portion 26 to move relative to the electrode main portion 24. This aspect of the preferred embodiment allows the physician to selectively alter the distance that the distal ends of the electrode needle portions 26 will extend beyond the corresponding electrode main portions 24 and into the ventricular wall or other tissue. In, for example, a probe that is intended to be used to form epicardial lesions on the left ventricular wall (which is typically about 10 to 20 mm thick), movement of the electrode needle portions 26 will be limited to the extent that their respective tips will extend no more than about 9 mm from the main portions 24.

The exemplary shaft 14 also includes a deflectable tip section 76 that facilitates precise placement of the electrodes 12. [Note FIGS. 1 and 7.] The tip section 76, which is mounted on the distal end of the hypotube 36, is connected to a slidable tab 78 on the handle 18 by a pull wire 80. The pull wire 80 is secured to an anchor ring 82 that is mounted in the distal end of the tip section 76. Proximal movement of the slidable tab 78 will cause the tip section 76 to deflect. Suitable materials for the tip section 76 include low durometer materials such as shore 80A polyurethane, silicone, etc.

Each electrode needle portion 26 is electrically coupled to an individual wire 84 (FIG. 5) to conduct lesion forming (i.e. coagulating) energy to them. The wires are passed through the tubular needle support elements 48 and then connected to a PC board 86 in the handle 18 (FIGS. 1 and 8), where they are electrically coupled to a connector 88 that is received in a port on the handle. The connector 88 plugs into the source of RF coagulation energy 20. The electrodes 12 are preferably operated in a uni-polar mode in which the soft tissue coagulation energy emitted by the electrodes is returned through an indifferent patch electrode (not shown) externally attached to the skin of the patient. The amount of power required to coagulate tissue ranges from 5 to 150 w, with about 10 to 50 w being preferable for epicardial lesion formation.

Temperature sensors (not shown), such as thermocouples or thermistors, may be located on the electrodes 12. Preferably, the temperature sensors are located in the distal section of the needle electrode 26. In some embodiments, a reference thermocouple may also be provided. For temperature control purposes, signals from the temperature sensors are transmitted to the source of coagulation energy by way of wires 90 (FIG. 5) that are also connected to the PC board 86. A suitable power control arrangement is disclosed in U.S. Pat. No. 6,071,281, which is entitled "Surgical Method and Apparatus For Positioning a Diagnostic of Therapeutic Element Within the Body" and incorporated herein by reference. The electrodes may also have a porous coating such as the regenerative cellulose coatings disclosed in U.S. Pat. No. 5,991,650, which is entitled "Surface Coatings for Catheters, Direct Contacting Diagnostic and Therapeutic Devices" and incorporated herein by reference.

The exemplary surgical probe 10 illustrated in FIGS. 1-9 may be used to in the following exemplary myocardial revascularization and denervation method. Access to the epicardial surface may first be obtained thoracoscopically or by way of another minimally invasive technique. The shaft 14 may then be inserted into the patient with the electrodes 12 and electrode support assembly 16 withdrawn in the manner illustrated in FIG. 7. In those instances where the shaft 14 is malleable, the shaft may first be bent into the shape desired by the physician. The distal end of the shaft 14 should be approximately 1 cm from the epicardial surface and positioned such that the distal end faces the target tissue region. More precise orientation of the distal end of the shaft 14 may be accomplished by deflecting the tip 76 with the slidable tab 78.

After the shaft 14 has been properly positioned, the electrode support assembly 16 may be urged outwardly from the distal end of the shaft using the slidable tab 58 until it reaches the extended position illustrated in FIGS. 1 and 6. The electrode main portions 24 should then engage the epicardial surface. If any distance remains between the electrodes 12 and the epicardial surface, the physician will simply advance the shaft 14 distally until contact is made. The electrode needle portions 26 may then be advanced through epicardial surface the desired distance into the ventricular wall (FIG. 3) with the slidable tab 68. At this point, power may be supplied to the electrodes 12 to form lesions in the manner illustrated in FIGS. 2 and 3. The electrode needle portions 26 may, alternatively, be held in their retracted positions and the lesion formed solely with the main portions 24. A typical procedure would involve the formation of 10 to 20 lesions.

Figure 10:
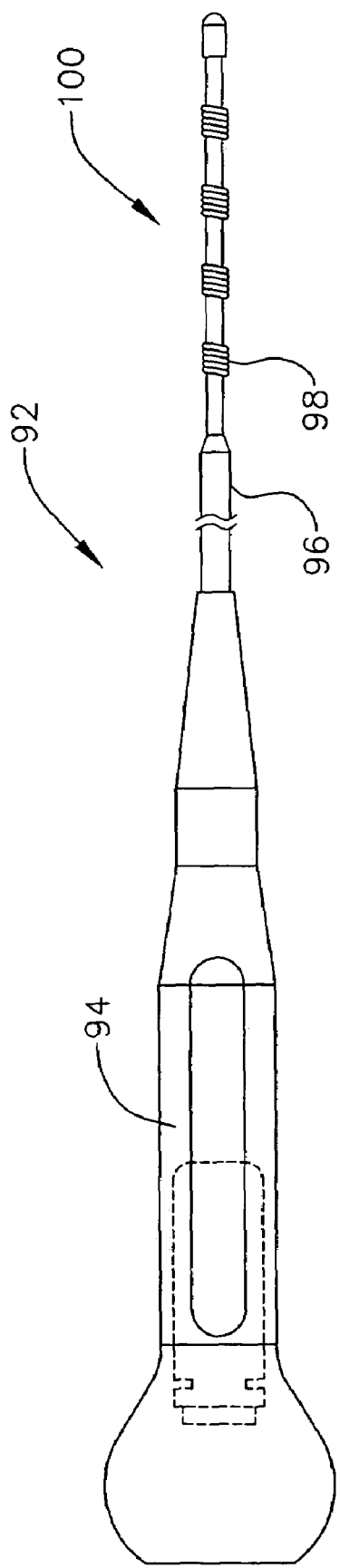
FIG. 10 is a plan view of an apparatus in accordance with a preferred embodiment of a present invention.

Another exemplary surgical probe 92 that may be used to form epicardial lesions in accordance with the present method is illustrated in FIG. 10. The probe is substantially similar to the probe illustrated in FIGS. 1–9 in that it includes a handle 94 and a relatively stiff shaft 96. Here, however, electrodes 98 are mounted on a shaft distal section 100 that is fixedly mounted on the end of the shaft 96. The shaft distal section 100 may be either somewhat flexible, in that it will conform to a surface against which it is pressed and then spring back to its original shape when removed from the surface, or malleable.

The electrodes 98 do not include a needle portion and, instead, are preferably spaced apart wound, spiral coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. The electrodes 98 are preferably about 2.5 to 5.0 mm in length and about 7 to 9 French in diameter and are separated by about 1 cm. Such size and spacing will result in a series of spaced lesions on the epicardial surface when used in a uni-polar mode.

Additional information concerning the probe illustrated in FIG. 10 may be found in aforementioned U.S. Pat. No. 6,071,281.

Although the present inventions have been described in terms of the preferred embodiments above, numerous modifications and/or additions to the above-described preferred embodiments would be readily apparent to one skilled in the art. It is intended that the scope of the present inventions extends to all such modifications and/or additions.

I claim:

1. A myocardial revascularization and denervation method, comprising the steps of:
    positioning an electrode, including an electrode main portion and an electrode needle portion, on the epicardial surface such that the electrode main portion is on the epicardial surface of a ventricle;
    piercing the epicardial surface with the electrode needle portion such that the electrode needle portion is located within the ventricular wall; and
    transmitting energy from the electrode, through the epicardial surface and into the ventricular wall to create a lesion within the ventricular wall.

2. A method as claimed in claim 1, wherein the step of transmitting energy from the electrode comprises transmitting energy from the electrode main portion and the electrode needle portion.

3. A myocardial revascularization and denervation method, comprising the steps of:
    positioning an electrode on the epicardial surface of a ventricle shaped such that the lesion produced thereby will define a first region relatively close to the epicardial surface with a relatively large cross-sectional area and a second region relatively far from the epicardial surface with a relatively small cross-sectional area; and
    transmitting energy from the electrode, through the epicardial surface and into the ventricular wall to create a lesion within the ventricular wall.

4. A method as claimed in claim 3, wherein the step of positioning an electrode on the epicardial surface of a ventricle comprises the step of introducing the electrode thoracoscopically.

5. A method as claimed in claim 3, wherein the step of positioning an electrode on the epicardial surface of a ventricle comprises positioning a plurality of electrodes on the epicardial surface of the ventricle.

6. A myocardial revascularization and denervation method for use on a wall of the heart defining an epicardial surface and an endocardial surface, the method comprising the steps of:
    positioning a first lesion creation device on the epicardial surface;
    positioning a second lesion creation device within the heart wall; and
    forming a lesion with the first and second lesion creation devices.

7. A method as claimed in claim 6, wherein the step of positioning a first lesion creation device on the epicardial surface comprises positioning an electrode on the epicardial surface.

8. A method as claimed in claim 6, wherein the step of positioning a second lesion creation device within the heart wall comprises positioning an electrode within the heart wall.

9. A method as claimed in claim 6, wherein the step of forming a lesion with the first and second lesion creation devices comprises forming a first lesion portion having a first cross-sectional area and a second lesion portion having a second cross-sectional area less than the first cross-sectional area.

10. A method as claimed in claim 9, wherein the step of forming a first lesion portion comprises forming a first lesion portion that extends inwardly from the epicardial surface towards the endocardial surface and the step of forming a second lesion portion comprises forming a second lesion portion that extends inwardly from the first lesion portion.

11. A method as claimed in claim 9, wherein the step of forming a lesion with the first and second lesion creation devices comprises forming a lesion which, when viewed in a cross-section taken in a plane perpendicular to the epicardial surface, includes a first area that defines a border having a relatively smooth slope, a second area that defines a border having a relatively smooth slope, and a abrupt change in slope therebetween.

* * * * *